(12) United States Patent
Carbonari

(10) Patent No.: US 8,771,250 B2
(45) Date of Patent: Jul. 8, 2014

(54) INVERSE STANDING GATHERS FOR AN ABSORBENT ARTICLE

(75) Inventor: Raquel Carbonari, Philadelphia, PA (US)

(73) Assignee: SCA Hygiene Products AB, Gothenburg (SE)

( * ) Notice: Subject to any disclaimer, the term of this patent is extended or adjusted under 35 U.S.C. 154(b) by 657 days.

(21) Appl. No.: 12/608,303

(22) Filed: Oct. 29, 2009

(65) Prior Publication Data

US 2011/0106038 A1   May 5, 2011

(51) Int. Cl.
  *A61F 13/15*   (2006.01)
  *A61F 13/20*   (2006.01)
(52) U.S. Cl.
  USPC .................................. 604/385.28; 604/385.01
(58) Field of Classification Search
  USPC ........... 604/385.24–385.28, 385.01, 385.101, 604/378
  See application file for complete search history.

(56) References Cited

U.S. PATENT DOCUMENTS

| | | | | |
|---|---|---|---|---|
| 4,636,207 A | * | 1/1987 | Buell | 604/370 |
| 4,701,177 A | * | 10/1987 | Ellis et al. | 604/385.26 |
| 4,865,597 A | * | 9/1989 | Mason et al. | 604/385.31 |
| 5,064,489 A | | 11/1991 | Ujimoto et al. | |
| 5,292,316 A | | 3/1994 | Suzuki | |
| 5,415,644 A | | 5/1995 | Enloe | |
| 5,624,425 A | | 4/1997 | Gray et al. | |
| 5,810,800 A | * | 9/1998 | Hunter et al. | 604/385.23 |
| 5,818,563 A | * | 10/1998 | Colgan et al. | 349/158 |
| 6,166,285 A | * | 12/2000 | Schulte et al. | 604/364 |
| 6,264,642 B1 | | 7/2001 | Kuen et al. | |
| 6,315,765 B1 | * | 11/2001 | Datta et al. | 604/385.24 |
| 6,458,113 B2 | * | 10/2002 | Kashiwagi | 604/385.16 |
| 6,468,257 B1 | * | 10/2002 | Ono et al. | 604/391 |
| 6,475,200 B2 | * | 11/2002 | Mizutani et al. | 604/385.01 |
| 6,569,140 B1 | | 5/2003 | Mizutani et al. | |
| 6,632,208 B1 | | 10/2003 | Mizutani | |
| 6,682,515 B1 | * | 1/2004 | Mizutani et al. | 604/385.27 |
| 7,462,174 B2 | | 12/2008 | Nishitani et al. | |
| 7,641,642 B2 | * | 1/2010 | Murai et al. | 604/385.28 |
| 2004/0236299 A1 | | 11/2004 | Tsang et al. | |
| 2008/0021433 A1 | | 1/2008 | Allison-Rogers | |
| 2008/0287904 A1 | | 11/2008 | Drevik et al. | |

FOREIGN PATENT DOCUMENTS

| | | |
|---|---|---|
| EP | 1 051 957 | 11/2000 |
| EP | 1 101 470 | 5/2001 |
| EP | 1 308 148 | 5/2003 |
| EP | 1 321 118 | 6/2003 |
| EP | 1 354 576 | 10/2003 |
| EP | 1 656 917 | 5/2006 |
| EP | 1 917 939 | 7/2008 |
| GB | 2 262 873 | 7/1993 |
| WO | WO-2004/105664 | 12/2004 |

\* cited by examiner

*Primary Examiner* — Michele M Kidwell
(74) *Attorney, Agent, or Firm* — Drinker Biddle & Reath LLP

(57) ABSTRACT

An absorbent article includes an a pair of leakage protection walls including a standing gather. The leakage protection walls are affixed to the backsheet or an outer layer of the article. Each standing gather is configured to be folded over side edges of the absorbent article so that each standing gather extends towards a user causing portions of the first and second end regions of the absorbent article to curve inwardly. In addition, the inverse standing gathers force laterally extending sides of the article to stand erect, thereby creating a double sealing effect. Attaching the leakage protection wall to the backsheet or outer layer of the article increases the inlet area, while also improving leakage.

21 Claims, 9 Drawing Sheets

INVERSE STANDING GATHERS FOR AN ABSORBENT ARTICLE

FIELD OF THE INVENTION

The present invention relates to leakage protection walls or standing gathers for an absorbent article. More particularly, the present invention relates to inverse standing gathers for an absorbent article.

BACKGROUND OF THE INVENTION

Leakage protection is an important feature for absorbent articles. Absorbent articles typically include a topsheet, a backsheet, and an absorbent core disposed therebetween. Other layers may also be included, such as an adhesive layer, transfer layer, a tissue layer, elastic layer or the like. To prevent side leakage of fluid, a leakage protection wall may be provided on a user facing side of the absorbent article. The leakage protection wall extends in a longitudinal direction of the absorbent article on the user facing side of the article, as shown for example, in FIG. 1.

Typically, the walls are disposed towards the user from the side longitudinal edges of the absorbent article, and are made of a sheet of material with elastic members applied to the sheet. The elastic members exert a contractive force to bring the rear and front surfaces of the article together. When the absorbent article is applied to an undergarment of the user, as in the case of a sanitary napkin, the wall rises further due to the elasticity of the sheet. In this way, end portions of the crotch portion rise against the wearer, giving a much more snug fit than an ordinary product known in the art. The standing gather elastics may also support leg elastics to give the product a better fit to the body of the wearer.

However, because the leakage protection walls are disposed on the user facing side of the article, the size of the inlet opening is decreased. In addition, the walls may become folded towards the center of the absorbent article, thereby further reducing the size of the inlet opening. Finally, liquid may leak along the hydrophilic top sheet, and may cause discoloration of the edge of the absorbent article and/or the wearer's pants.

Accordingly, there is a need in the art for a leakage protection wall that avoids the disadvantages of the prior art.

SUMMARY

According to a first aspect of the invention, an absorbent article has a first end region and a second end region and includes a liquid permeable topsheet, a liquid impermeable backsheet, an absorbent core disposed therebetween, and a pair of leakage protection walls. The leakage protection walls extend in a longitudinal direction of the absorbent article and are affixed to the backsheet or an outer layer of the article. Each of the leakage protection wall are made of a sheet. Each said sheet includes a standing portion, wherein at least a portion of one edge region of the standing portion is secured to the backsheet or outer layer while the other edge region of the standing portion comprises elastic members. Each of the standing portions is configured to be folded over side edges of the absorbent article so that each standing portion extends towards the user causing portions of the first and second end regions of the article to curve towards the user.

According to a second aspect of the invention, a method of manufacturing an absorbent article includes providing an absorbent article with a liquid permeable topsheet, a liquid impermeable backsheet, and an absorbent core disposed therebetween. A pair of leakage protection walls are attached on the backsheet or an outer layer of the article. Each of the leakage protection walls extend in a longitudinal direction of the absorbent article and are affixed to the backsheet or outer layer. Each of the leakage protection walls are made of a sheet. Each sheet includes a standing portion. At least a portion of one edge region of the standing portion is secured to the backsheet or outer layer while the other edge region of the standing portion comprises elastic members. Each standing portion is configured to be folded over side edges of the absorbent article so that each standing portion extends towards the user causing portions of the first and second end regions of the article to curve towards the user.

According to a third aspect, a belted undergarment, brief, or pant-type absorbent article includes a liquid permeable topsheet, a liquid impermeable backsheet, an absorbent core disposed therebetween, leg elastics disposed between said topsheet and said backsheet, and a pair of leakage protection walls. The leakage protection walls extend in a longitudinal direction of the absorbent article and are affixed to the backsheet or an outer layer of the article. Each leakage protection wall is made of a sheet. Each sheet includes a standing portion, wherein at least a portion of one edge region of the standing portion is secured to the backsheet or outer layer while the other edge region of the standing portion comprises elastic members. Each standing portion is configured to be folded over side edges of the absorbent article so that each standing portion extends towards the user causing portions of the first and second end regions of the article to curve towards the user. The standing portion and the leg elastics create a double sealing effect in at least the crotch region of the article.

A further feature of the first and second aspects is that a width of the first end region of the article is greater than a width of a central portion a crotch portion and a width of the second end region of the article.

Yet a further feature of the first and second aspects is that a width of the first end region of the article and a width of the second end region article is greater than a width of a central portion of a crotch portion.

Still yet a further feature of the first and second aspects is that each sheet includes first and second fixation portions, the sheet being secured therebetween.

Still yet another feature of the first and second aspects is that the leakage protection walls are formed as part of the backsheet.

Still yet a further feature of the first and second aspects is that the leakage protection walls are formed as a single layer.

Still yet a further feature of the first and second aspects is that the leakage protection walls are formed as a multilayer.

Still yet a further feature of the first and second aspects is that adhesive is disposed on an outer surface of the standing portion to attach to a leg of a user.

Yet still another feature of the first and second aspects is that the topsheet and backsheet include portions extending laterally beyond the absorbent core, the laterally extending portions being positioned towards the user and adjacent said standing gather to create a double sealing effect.

Still yet a further feature of the second aspect is that the absorbent article is attached to a continuous body portion to form a pant.

Yet still another feature of the second aspect is that the absorbent article is attached to first and second end panels to form a belted undergarment, brief or pant type absorbent article.

Still yet a further feature of the first, second and third aspects is that the leakage protection walls are positioned at least 5 mm from a longitudinal edge region of the backsheet.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements.

DETAILED DESCRIPTION OF THE PREFERRED EMBODIMENTS

Figure 1:
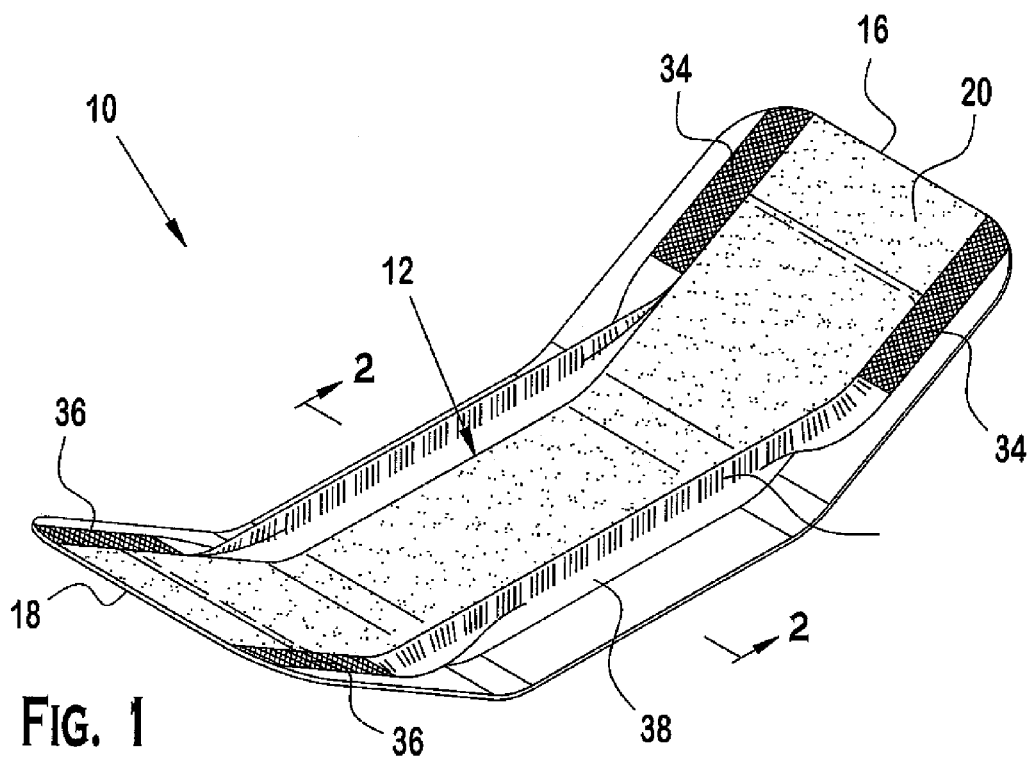
FIG. 1 is a perspective view of a sanitary napkin including a standing gather according to the prior art.
Figure 2:
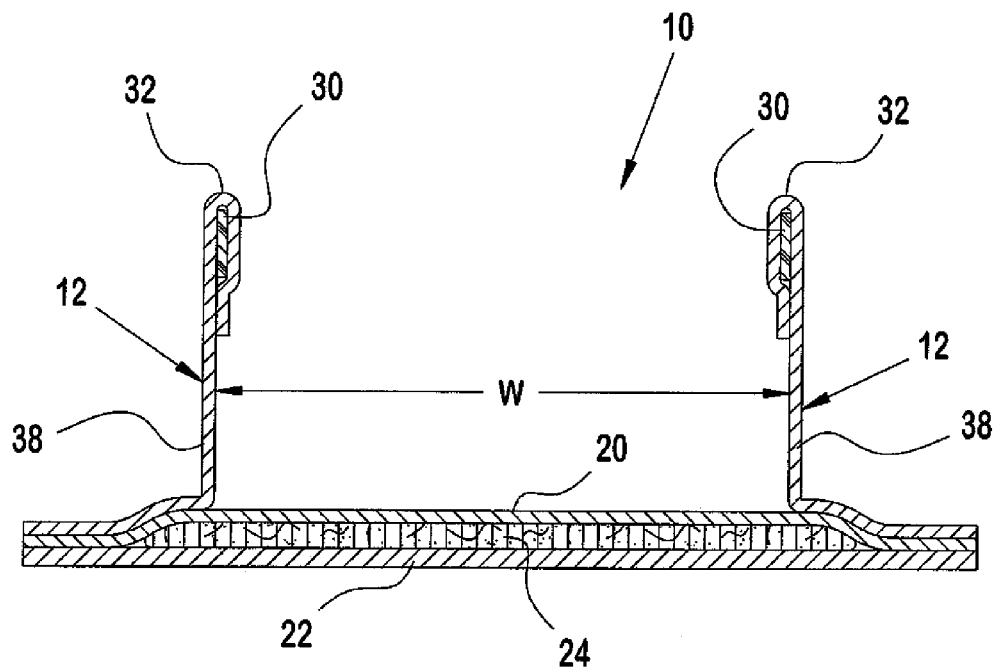
FIG. 2 is a cross sectional view of the standing gather taken along line 2-2 of FIG.

With reference to FIGS. 1 and 2, a prior art sanitary napkin 10 includes a pair of leakage protection walls 12 disposed in a longitudinal direction of the sanitary napkin 10. The leakage protection walls 12 extend from a first end region 16 of the napkin 10 to a second end region 18 of the napkin 10, as shown, for example, in FIG. 1. The first end region 16 and the second end region 18 can be either the rear or front portion of the napkin 10.

With reference to FIG. 2, the sanitary napkin 10 includes a liquid, permeable topsheet 20, a liquid, impermeable backsheet 22, and an absorbent core 24 disposed therebetween. The leakage protection walls 12 are affixed to the topsheet 20 of the sanitary napkin 10, and may be comprised of a semi-permeable sheet. Each sheet 12 includes an elastic member 30 extending along at least a portion of a distal edge region 32 of the sheet 12.

With reference to FIG. 1, each sheet 12 includes a first fixation portion 34 and a second fixation portion 36, which are affixed to the topsheet 20 so that the sheet 12 lies flat at these locations. With reference to FIGS. 1 and 2, a standing portion 38 extends between the first fixation portion 34 and second fixation portion 36 of each sheet 12. The sheet 12 is configured so that the elastic member 30 forces the first end region 16 and the second end region 18 towards the user while the standing portion 38 stands erect. As described above, the width W of the inlet area of the napkin 10 on the topsheet 20 (as shown in FIG. 2) is decreased in size, due to the placement of the leakage protection walls 12 on the topsheet 20.

With reference to FIGS. 3A, 3B, 3C, 4, and 5, a first embodiment of an absorbent article in accordance with the present invention is described in more detail. An absorbent article is defined as an article used for the absorption of body fluids, including but not limited to, infant diapers and training pants, adult incontinence products, feminine hygiene products, and gender specific absorbent products. While FIGS. 3A, 3B, 3C, 4, and 5 specifically illustrate a sanitary napkin 110, the features of the present invention can be applied to all types of absorbent articles for the absorption of body fluids.

Figure 4:
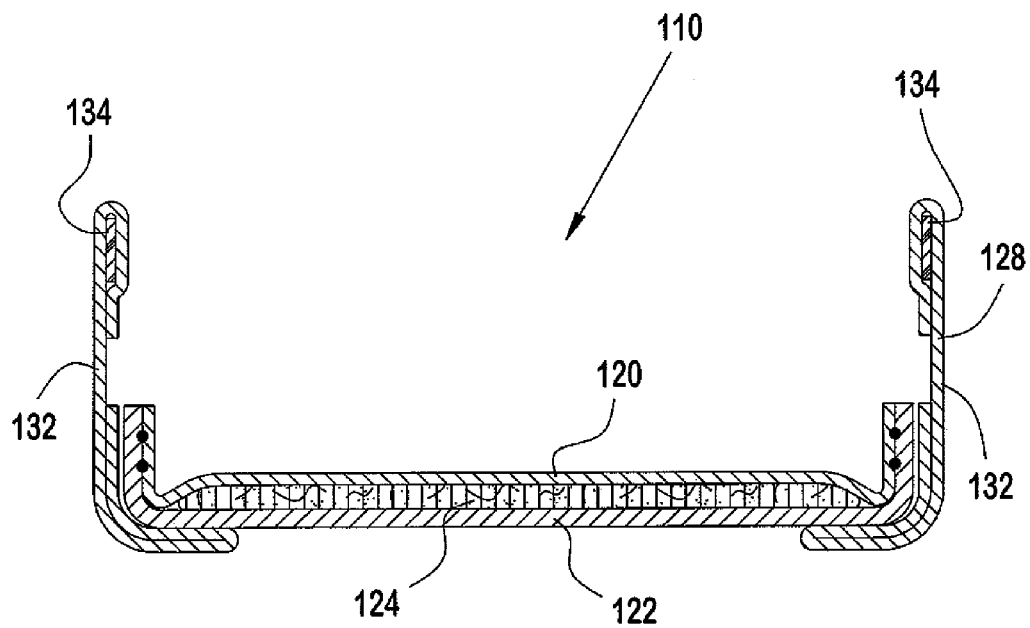
FIG. 4 is a cross sectional view of the inverse standing gather taken along line 4-4 of FIG. 3A according to the present invention.

With reference in particular to FIG. 4, a sanitary napkin 110 includes a liquid permeable topsheet 120, a liquid impermeable backsheet 122 and an absorbent body 124 enclosed therebetween. It should be understood that the absorbent article of the present invention may include various intervening layers, such as an adhesive layer, transfer layer, tissue layer, and/or an elastic layer, for example. Moreover, it should also be understood that the topsheet, backsheet and absorbent body may be made of multilayers, and varying materials, as is known in the art.

The liquid permeable topsheet 120 may be made from a nonwoven material, e.g., spunbonded, meltblown, carded, hydroentangled, wetlaid etc. Suitable nonwoven materials can be composed of natural fibers, such as woodpulp or cotton fibers, manmade fibers, such as polyester, polyethylene, polypropylene, viscose etc. or from a mixture of natural and manmade fibers, or tow fibers. Further examples of topsheet materials are porous foams, apertured plastic films etc. The materials suited as topsheet materials should be soft and non-irritating to the skin and be readily penetrated by body fluid, e.g., urine or menstrual fluid.

The liquid impermeable backsheet 122 may be made from a thin plastic film, e.g., a polyethylene or polypropylene film, a nonwoven material coated with a liquid impervious material, a hydrophobic nonwoven material, which resists liquid penetration or laminates of plastic films and nonwoven materials. The backsheet material may be breathable so as to allow vapor to escape from the absorbent core, while still preventing liquids from passing through the backsheet material.

Preferably, the topsheet 120 and the backsheet 122 extend outside the edges of the absorbent body 124, as shown for example, in FIG. 4. The layers 120 and 122 may be connected to each other within the extended portions thereof, e.g., by gluing or welding by heat or ultrasonic. The topsheet 120 and/or the backsheet 122 may further be attached to the absorbent core 124 by any method known in the art, such as adhesive, heatbonding etc. The absorbent core 124 may also be unattached to the topsheet 120 and/or the backsheet 122.

The absorbent core 124 may be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid receiving capacity, liquid distribution capacity and storage capacity. The thin absorbent bodies, which are common in for example baby diapers and incontinence guards, often include a compressed mixed or layered structure of cellulosic fluff pulp and superabsorbent. The size and absorbent capacity of the absorbent core may be varied to be suited for different uses such as baby diapers, adult incontinence diapers and pads, pant diapers, pantiliners, sanitary napkins etc.

Figure 3A:
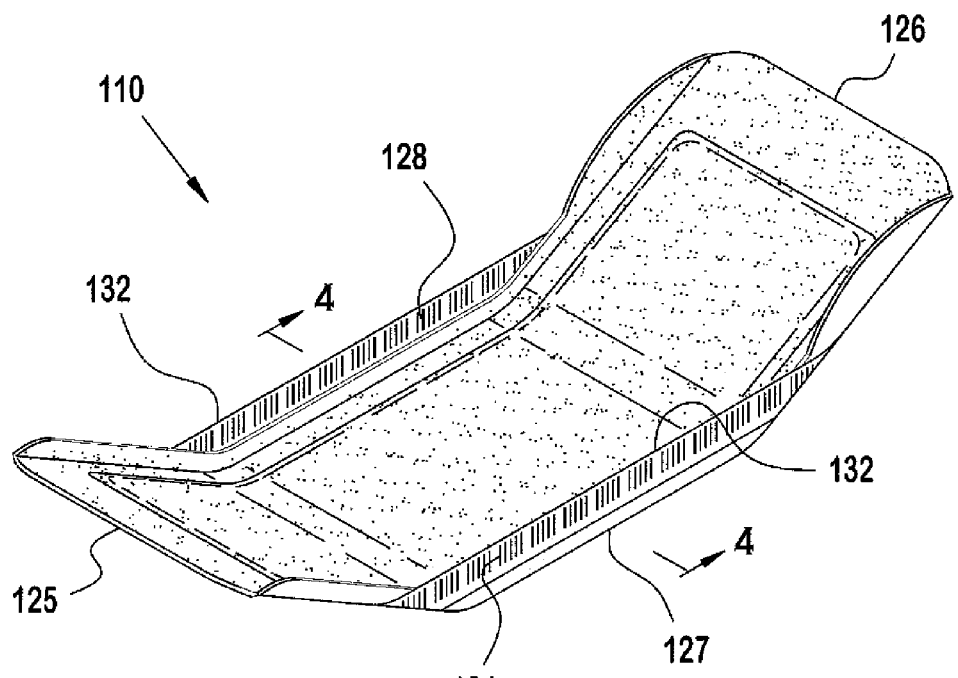
FIG. 3A is a perspective view of the inverse standing gather on an absorbent article according to the present invention.
Figure 3B:
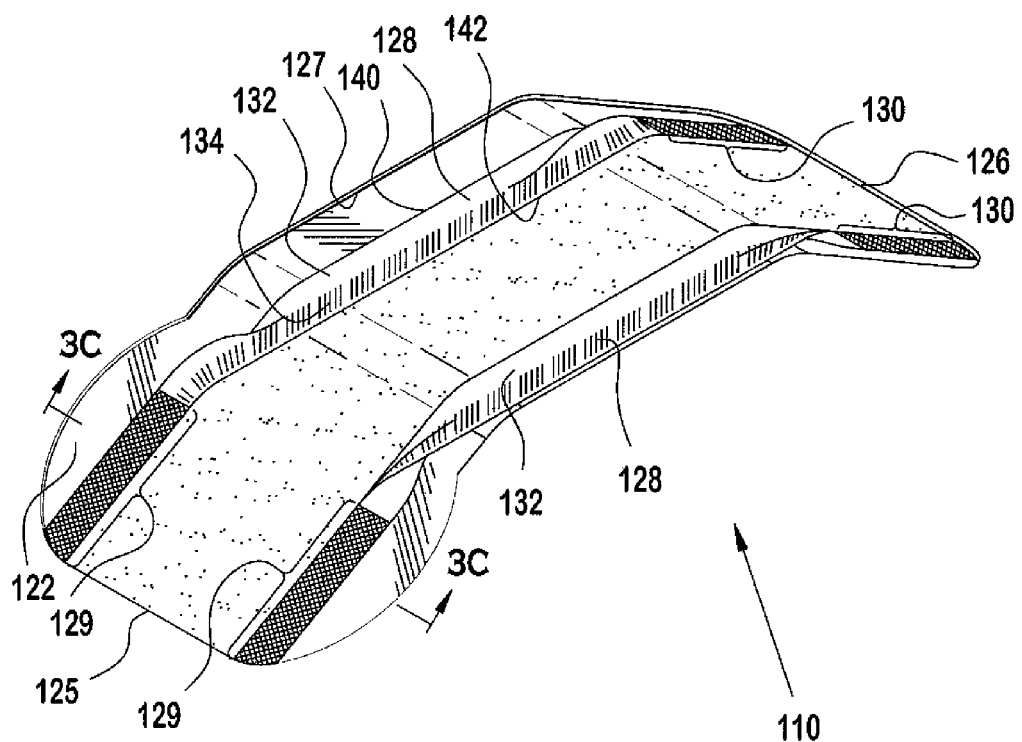
FIG. 3B is a perspective view of the inverse standing gather in a non-extended position on an absorbent article according to the present invention.

With reference to FIGS. 3A and 3B, the sanitary napkin 110 includes a first end region 125 and a second end region 126 and a crotch portion 127 therebetween. The first end region 125 and the second end region 126 can be either the rear or front end of the napkin 110. Preferably, one of the first end region 125 and second end region 126 or both are wider than a central portion of crotch portion 127. In the case where both the first end region 125 and second end region 126 are wider, an hour-glass shape may be formed, as shown for example in FIG. 3B.

To further aid in leakage protection, a leakage protection wall 128 is provided, as shown in FIGS. 3A, 3B, 4 and 5. With reference to FIG. 3B, a pair of leakage protection walls 128 are shown in a non-extended position. In particular, the leakage protection walls 128 are affixed to the backsheet 122 of the napkin 110 (or any outer layer of the article), and extend in a longitudinal direction of the sanitary napkin 110. Each leakage protection wall 128 is made from a sheet of material.

Preferably, the leakage protection walls 128 are made from a nonwoven material and may be permeable, semipermeable or impermeable, depending on design preference. In addition, the walls may be made from a single layer of material, or multiple layers of material. The single layer of material may be comprised of a multilayer nonwoven, such as SSS, SMS, or a bi-component. However, the leakage protection walls 128 can be made from any other material, depending on design preference. Preferably, the weight of the material can range from 8-24 gsm, and most preferably around 12 gsm. However, higher or lower weights are also possible.

Preferably, each sheet 128 includes a first fixation portion 129 and second fixation portion 130. The first fixation portion 129 and second fixation portion 130 of each sheet 128 are preferably secured along their width to the backsheet 122, so that the first fixation portion 129 and second fixation portion 130 lie parallel or flat against the back sheet 122. However, other configurations are possible. For example, only a portion of the width of each sheet 128 may be secured along the fixation portions 129 and 130. In addition, the sheets need not extend between the first end region 125 of the napkin 110 to the second end region 126 of the napkin 110, but rather can be spaced from the ends.

Figure 3C:
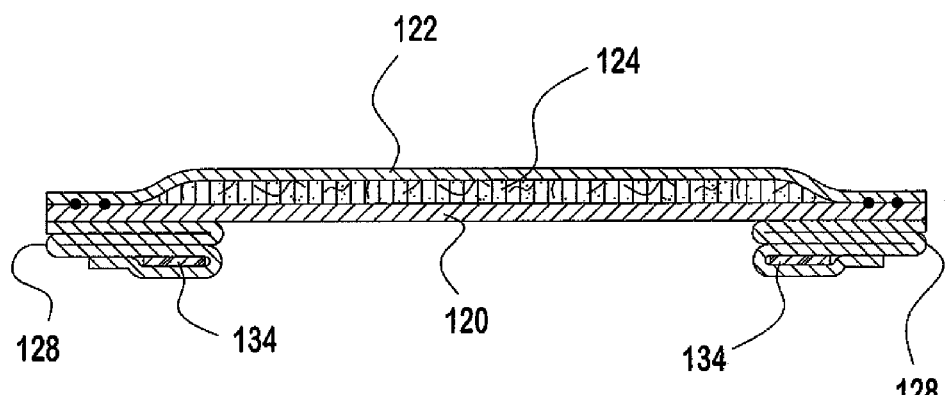
FIG. 3C is a cross sectional view of the absorbent article taken along line C-C of FIG. 3B according to the present invention.

In the preferred embodiment, the sheet 128 may be triple folded and then bonded as shown for example, in FIG. 3C. However, the sheet 128 need not be triple folded, but can have a single fold or double folds, or any other amount of folds depending on application and design preference. In addition, the fixation portions 129 and 130 may be asymmetrical. For example, in male products, the absorbent core is wider in the front, and in female products, wider in the back. As such, depending on the application, the fixation portion may be asymmetrical. In addition, the leakage protection walls 128 may be secured to the backsheet 122 in various ways, such as in a straight line, curved line, or in any other pattern.

With reference to FIG. 3B, each sheet 128 includes a standing portion 132, wherein one edge region 140 of the standing portion 132 is secured to the backsheet 122 while the other edge region 142 of the standing portion 132 includes an elastic member or members 134. That is, at least a lengthwise portion of one edge region 140 of the standing portion 132 is secured to the backsheet 122, i.e, the joined edge region, while at least a portion of the other edge region 142, i.e., the distal edge region, includes elastic members 134 extending thereon. Preferably, the joined edge region 140 of standing portion 132 is bonded (glued, heat sealed, ultrasonically bonded, et) to the backsheet 122 at least 5 mm from an edge region of the backsheet 122. In addition, the standing portion preferably extends at least 100 mm along the longitudinal length of the article in the crotch region. Moreover, the bonded material ratio is preferably between 30-70%. The bonded material ratio is calculated by adding the length L1 of the fixation portion 129 with the length L2 of the fixation portion 130 and dividing that sum by the total length of the standing portion 132. Preferably, inner edge of the fixation portion 129 should be distanced from the inner edge of fixation portion 130 by at least 50 mm.

Figure 5:
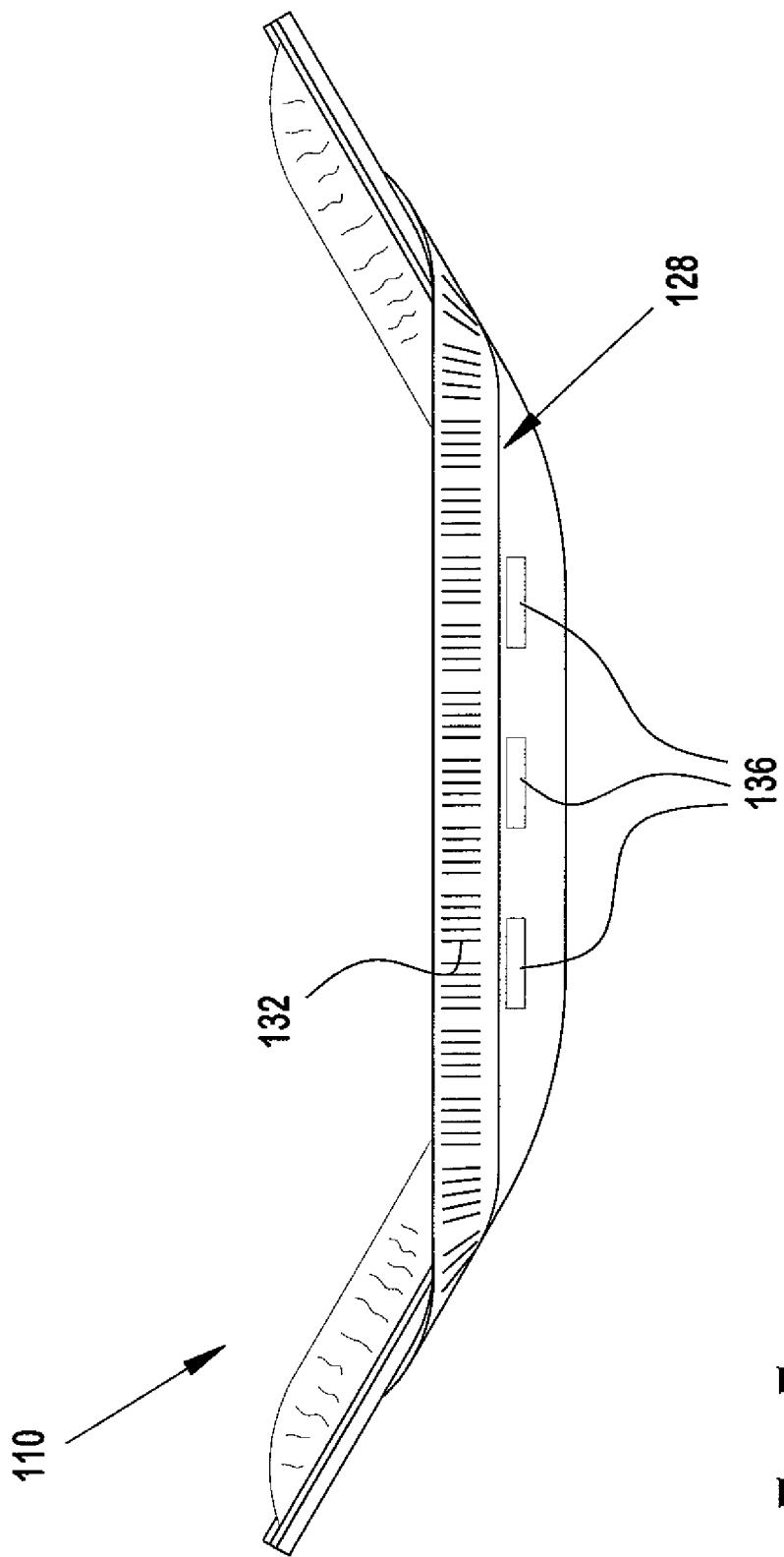
FIG. 5 is a side elevational view of the inverse standing gather according to the present invention.

When in a non-extended position as shown in FIG. 3B, the elastic member(s) 134 function to exert a contractive force to bring the first end region 125 and second end region 126 of the napkin together, but in an inverted position. That is, the first end region and second end region would contract away from a user, rather than towards a user. With reference to FIGS. 3A, 4 and 5, the standing portions 132 of the sanitary napkin 110 are shown in an extended, use position. In particular, each standing portion 132 is folded over itself (FIG. 5) and over side edges of the napkin 110 so that the standing portion 132 stands erect. The contractive force of the standing portion 132 causes the portions of the top sheet and back sheet extending beyond the absorbent core 124 to stand erect, as shown in FIG. 4, in addition to the standing portion 132. This creates a double sealing effect.

Further, the contractive force causes a wider side edge of the first end region 125 and second end region 126 of the sanitary napkin 110 to curve towards the user, as shown for example, in FIG. 3A. That is, during use, the first and second end regions 125, 126 will be forced toward the wearer. In this way, the leakage protection walls are not affixed to the top sheet 120 but rather the back sheet 122, thereby maximizing the absorption inlet of the napkin 110. As such, the leakage protection is maximized, as the ability for fluid to leak out laterally is minimized.

With reference to FIG. 5, the outer surface of the standing gather 132 may be provided with an adhesive or adhesive strips 136. An adhesive may be positioned at various locations along the outer surface of the standing gather 132, so that it adheres to the inner leg of the wearer, depending on application and design preference.

While the napkin 110 is illustrated without wings, it should be understood that wings can be applied thereon. In this case, the wings will be affixed to the backsheet, while allowing the standing gathers to remain free. Preferably, the bond of the wing material to the pad needs to be at a distance from the crotch equal to or less than the distance where the standing portion is bonded to the backsheet.

Figure 6:
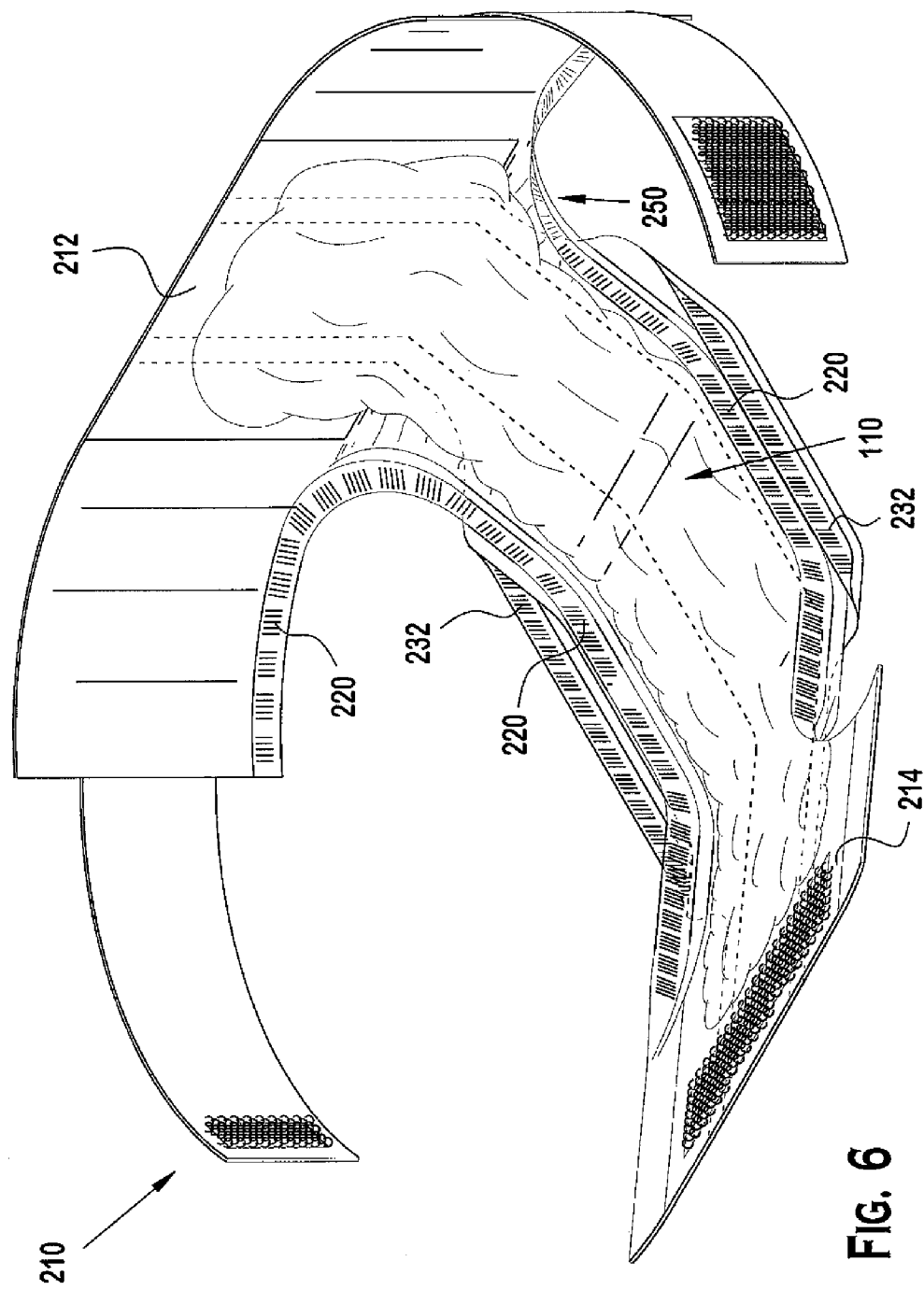
FIG. 6 is a perspective view of the inverse standing gather on a belted undergarment according to the present invention.

With reference to FIG. 6, the absorbent article of the present invention is shown as used in connection with a belted undergarment. In particular, the belted undergarment 210 includes an absorbent article similar in configuration to the sanitary napkin 110, except that the article is secured between first and second end panels 212 and 214 (not shown in FIG. 6) of the belted undergarment 210. In addition, the particular size of the absorption portion of the belted undergarment 210 will vary from the size of the sanitary napkin 110, depending on application and design preference.

The belted undergarment 210 includes leg elastics 220. Any type of leg elastics may be present, as is known in the art. For example, elastics may be placed at strategic locations on the article, particularly along the edges, or an elastic layer may be included. A pair of standing portions 232 are affixed to the backsheet of the pant 210, and configured to be folded over the leg elastics 220. The pair of standing portions 232 as applied to a belted undergarment preferably extend along only a portion of the article, and not the ends of the article.

When in an extended, use position, the standing portions 232 will exert a force on the leg elastics 220 to thereby force the leg elastics upward and create a double sealing effect in the crotch region, as shown, for example, in FIG. 6. In effect, the standing portions 232 will become the leg elastics 220. However, in the upper leg region in areas where the standing gathers 232 are not present (see, e.g., location 250), the leg elastics 220 will function to hold the product securely in place. Preferably, the heights of the standing portions 232 are larger than the heights of any gathers created by the product elastics 220 along the side edge regions of the article.

Figure 7:
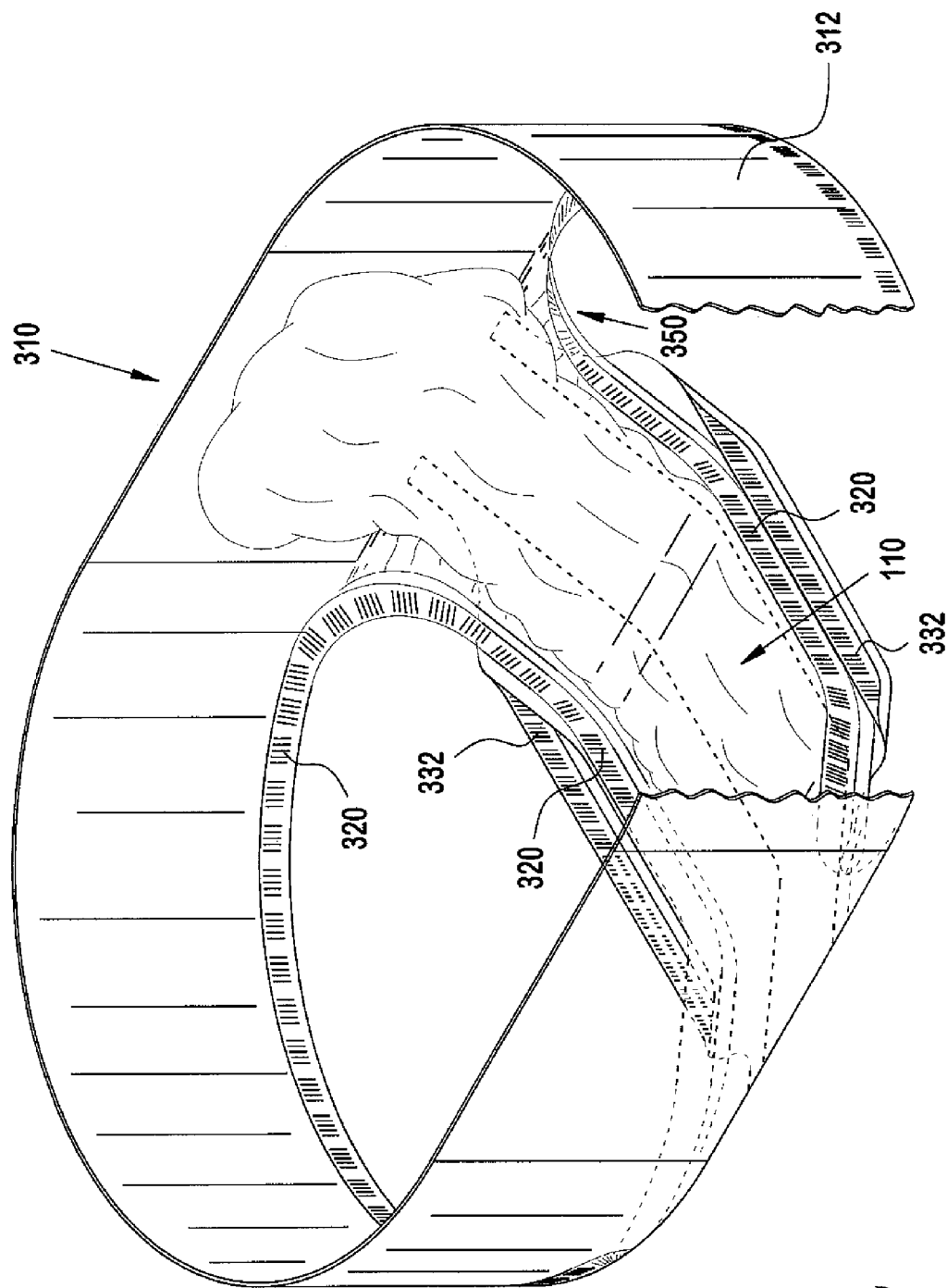
FIG. 7 is a perspective view of the inverse standing gather on a pant according to the present invention.

Similarly, with reference to FIG. 7, the absorbent article of the present invention is shown as used in a pant. In particular, the pant 310 includes an absorbent portion similar to that described in connection with the belted undergarment, except that the article has a closed waist 312 (not shown in FIG. 7). Some pants have elastic threads and others are made out of a full elastic film. In addition, the particular size of the absorption portion of the pant 310 will vary from the size of the sanitary napkin 110, depending on application and design preference.

The pant 310 may include leg elastics 320, but need not includes such leg elastics. Any type of leg elastics may be present, as is known in the art. For example, elastics may be placed at strategic locations on the article, particularly along the edges, or an elastic layer may be included. A pair of standing portions 332 are affixed to the backsheet of the pant 310, and configured to be folded over the leg elastics 320. However, it should also be understood that the standing portions 332 need not be attached directly to the backsheet of the pant 310, but rather could also be affixed to a hydrophobic layer of the pant, such as the insert P.E. or the innermost nonwoven in the chassis. In the case of no leg elastics, the standing portions 332 will be folded over the side edge of the pant. The standing portions 332 as applied to a pant preferably extend along only a portion of the article, and preferably not the ends of the article.

When in an extended, use position, the standing portions 332 will exert a force on the leg elastics 320 (or side edges of the pant) to thereby force the leg elastics (or side edges) upward and create a double sealing effect in the crotch region where leg elastics 320 are present, as shown, for example, in FIG. 7. If leg elastics are not present, the standing gathers would force the chassis upward, creating a double sealing effect. However, in the upper leg region in areas where the standing gathers 332 are not present (see, e.g., location 350), the leg elastics 320 will function to hold the product securely in place. Preferably, the heights of the standing portions 332 are equal to or larger than the heights of any gathers created by the product elastics 320 along the side edge regions of the article.

Figure 8:
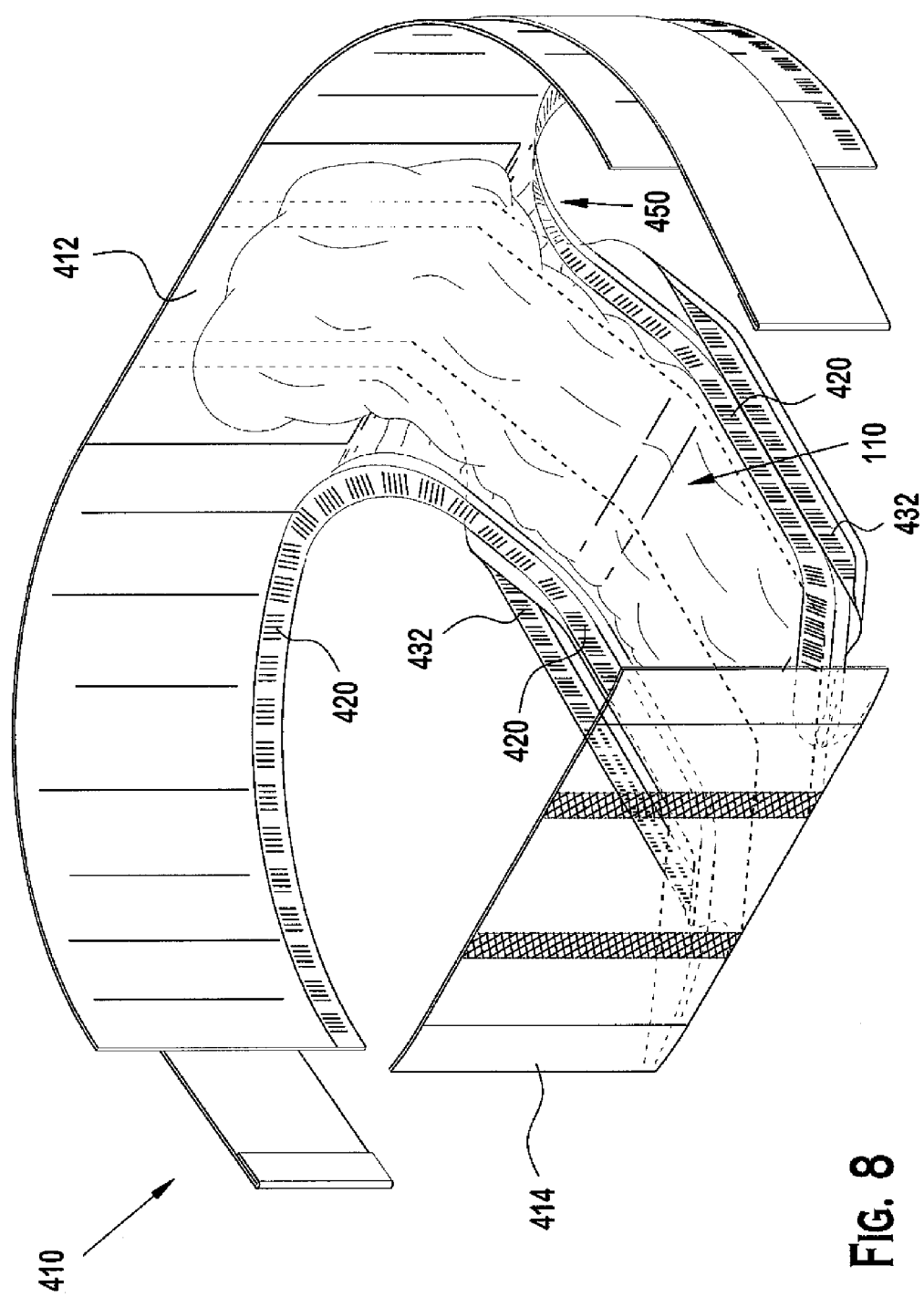
FIG. 8 is an alternative embodiment of the inverse standing gather on a brief according to the present invention.

With reference to FIG. 8, the absorbent article of the present invention is shown as used in a brief. In particular, the brief 410 includes an absorption portion secured between first and second end panels 412 and 414 (not shown in FIG. 8). The particular size of the absorption portion of the brief 410 will vary from the size of the sanitary napkin 110, depending on application and design preference.

As a belted undergarment, the brief includes leg elastics 420. Any type of leg elastics may be present, as is known in the art. For example, elastics may be placed at strategic locations on the article, particularly along the edges, or an elastic layer may be included. A pair of standing portions 432 are affixed to the backsheet of the brief 410, and configured to be folded over the elastic leg elastics 420. The standing portions 432 as applied to a diaper preferably extend along only a portion of the diaper, and not the ends of the diaper.

When in an extended, use position, the standing portions 432 will exert a force on the leg elastics 420 to thereby force the leg elastics 420 upward and create a double sealing effect in the crotch region. In effect, the standing portions 432 will become the leg elastics. However, in the upper leg region in areas where the standing gathers 432 are not present (see, e.g., location 450), the leg elastics 420 will function to hold the product securely in place. Preferably, the heights of the standing portions 432 are larger than the heights of any of the leg elastics 420 along the side edge regions of the brief 410.

Figure 9:
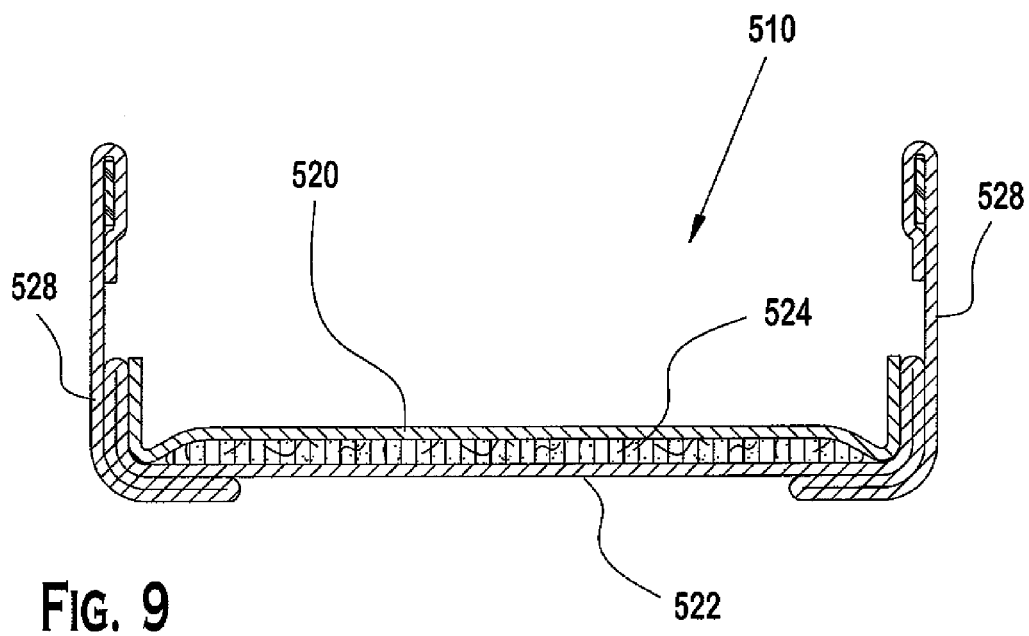
FIG. 9 is a cross sectional view of an alternative embodiment of the standing gather according to the present invention.
Figure 10:
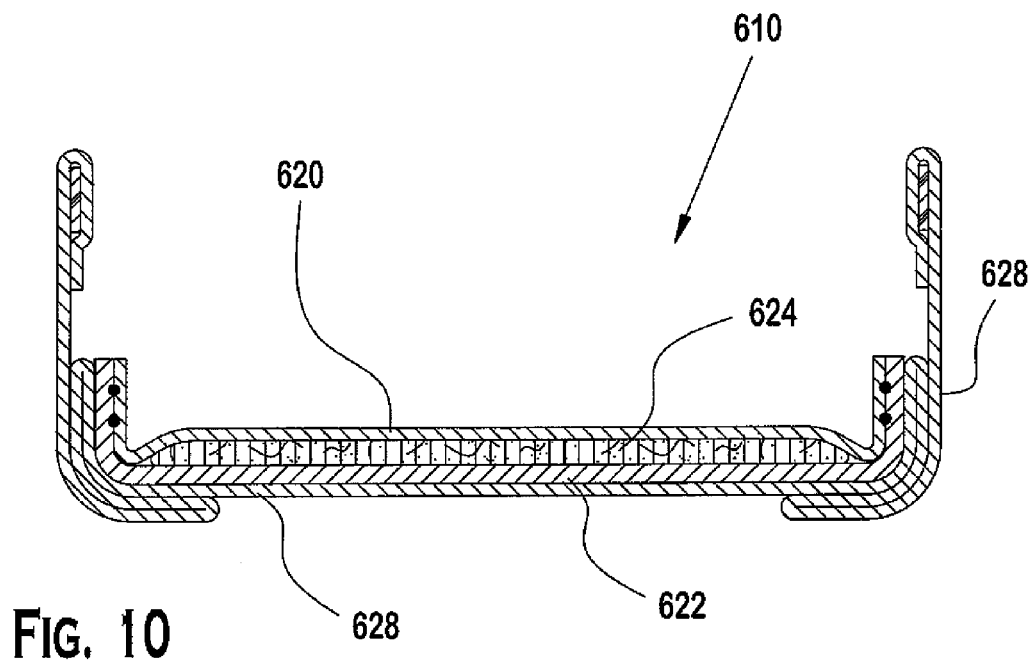
FIG. 10 is a cross sectional view of yet another alternative embodiment of the standing gather according to the present invention.
Figure 11:
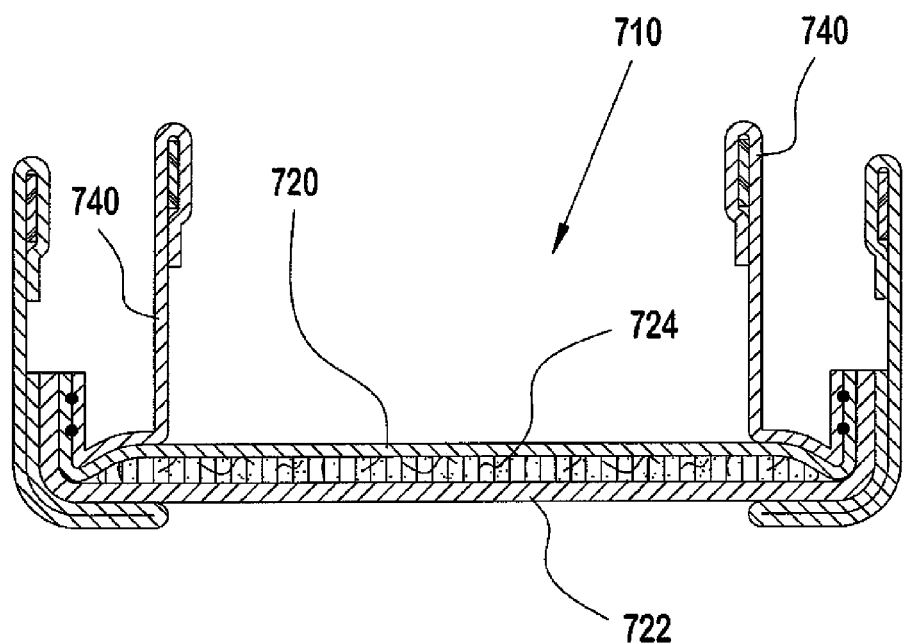
FIG. 11 is a cross sectional view of a further alternative embodiment of the standing gather according to the present invention including a standing gather of the prior art.

With reference to FIGS. 9-11, various configurations of the leakage protection walls of the present invention will be described in more detail. FIGS. 9-11 are cross sectional views of the leakage protection walls of the present invention, shown in an extended, use position. With reference to FIG. 9, an absorbent article 510 includes a top sheet 520 and back sheet 522 which sandwich an absorbent core 524 therebetween. The absorbent article 510 is similar in configuration to the napkin 110, except that the leakage protection wall 528 is formed from the back sheet 522, and is not separate therefrom. In addition, the leakage protection walls 528 may also be applied to the belted undergarment 210, pant 310 and brief 410, described above.

With reference to FIG. 10, an absorbent article 610 includes a top sheet 620 and back sheet 622 which sandwich an absorbent core 624 therebetween. The absorbent article 610 is similar in configuration to the napkin 110, except that the leakage protection walls 628 are formed as a single layer, and affixed along the entire outer surface of the back sheet. In addition, the leakage protection walls 628 may also be applied to the belted undergarment 210, pant 310 and brief 410, described above. It should be understood that the leakage protection walls 628 may be preassembled to the backsheet 622 before applying to the absorbent core 624.

With reference to FIG. 11, an absorbent article 710 includes a top sheet 720 and back sheet 722 which sandwich an absorbent core 724 therebetween. The absorbent article 710 is similar in configuration to the napkin 110, except that it also includes a standing gather 740 of the prior art, as shown for example, in FIGS. 1 and 2. In accordance with this configuration, additional leakage protection may be provided to existing standing gather designs, including those described above in connection with belted undergarments 210, pants 310 and brief 410.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. An absorbent article comprising:
   a liquid permeable topsheet;
   a liquid impermeable backsheet;
   an absorbent core disposed therebetween; and
   a pair of leakage protection walls, said leakage protection walls extending in a longitudinal direction of the absorbent article and affixed to a side facing away from the user of either the backsheet or a layer further than the backsheet from the user of the article, both leakage protection walls having a distal edge region and a proximal edge region, the distal edge region and the proximal edge region extending over an entire longitudinal extension of the absorbent core, both leakage protection walls including a standing portion arranged in a center area of the longitudinal extension, and first and second end portion arranged at respective ends of the longitudinal extension, the distal edge region having an elastic member, wherein the proximal edge region of the standing portion is secured to the side facing away from the user of either the backsheet or the layer further than the backsheet from the user, the first and the second end portions of said protection walls being folded and bonded to the side of the absorbent article facing away from the user, such that the distal edge region is arranged at the side facing away from the user in an area of the first and second end portions, wherein the distal edge region of the standing portion is arranged at the side of the absorbent article facing towards the user and extends towards the user causing portions of the first and second end regions of the article, to curve towards the user.

2. The absorbent article of claim 1, wherein a width of the first end region of the article is greater than a width of a central portion of a crotch portion and a width of the second end region of the article.

3. The absorbent article of claim 1, wherein a width of the first end region of the article and a width of the second end region of the article is greater than a width of a central portion of a crotch portion.

4. The absorbent article of claim 1, wherein each said sheet includes first and second fixation portions, said sheet being secured therebetween.

5. The absorbent article of claim 1, wherein the leakage protection walls are formed as part of the backsheet.

6. The absorbent article of claim 1, wherein the leakage protection walls are formed as a single layer.

7. The absorbent article of claim 1, wherein the leakage protection walls are formed as a multilayer.

8. The absorbent article of claim 1, wherein adhesive is disposed on an outer surface of the standing portion to attach to a leg of a user.

9. The absorbent article of claim 1, wherein said topsheet and backsheet include portions extending laterally beyond the absorbent core, said laterally extending portions being positioned towards the user and adjacent said standing gather to create a double sealing effect.

10. The absorbent article of claim 1, wherein the leakage protection walls are positioned at least 5 mm from a longitudinal edge region of the backsheet.

11. A method of manufacturing an absorbent article, comprising:
providing an absorbent article with a liquid permeable topsheet, a liquid impermeable backsheet, and an absorbent core disposed therebetween;
attaching a pair of leakage protection walls on a side facing away from the user of either the backsheet or a layer further than the backsheet from the user of the article, each said leakage protection walls extending in a longitudinal direction of the absorbent article and affixed to the side facing away from the user of either the backsheet or the layer further than the backsheet from the user, both leakage protection walls having a distal edge region and a proximal edge region, the distal edge region and the proximal edge region extending over an entire longitudinal extension of the absorbent core, both leakage protection walls including a standing portion arranged in a center area of the longitudinal extension, and first and second end portions arranged at respective ends of the longitudinal extension, the distal edge region having an elastic member, wherein the proximal edge region of the standing portion is secured to the side facing away from the user of either the backsheet or the layer further than the backsheet from the user; and
folding and bonding the first and second end portions to the side of the absorbent article facing away from the user, such that the distal edge region is arranged at the side facing away from the user in an area of the first and second end portions so that the distal edge region of the standing portion is arranged at the side of the absorbent article facing the user and extends towards the user causing portions of the first and second end regions of the article to curve towards the user.

12. The method of claim 11, wherein a width of the first end region of the article and a width of the second end region of the article is greater than a width of a central portion of a crotch portion.

13. The method of claim 11, wherein a width of the first end region of the article is greater than a width of a central portion of a crotch portion and a width of the second end region of the article.

14. The method of claim 11, wherein the leakage protection walls are formed as part of the backsheet.

15. The method of claim 11, wherein the leakage protection walls are formed as a single layer.

16. The method of claim 11, wherein the leakage protection walls are formed as a multilayer.

17. The method of claim 11, wherein adhesive is disposed on an outer surface of the standing gathers to attach to a leg of a user.

18. The method of claim 11, wherein said topsheet and backsheet include portions extending laterally beyond the absorbent core, said laterally extending portions being positioned towards the user and adjacent said standing gather to create a double sealing effect.

19. The method of claim 11, wherein the absorbent article is attached to a continuous body portion to form a pant.

20. The method of claim 11, wherein the absorbent article is attached to first and second end panels to form a belted undergarment, brief, or pant-type absorbent article.

21. The method of claim 11, wherein the leakage protection walls are positioned at least 5 mm from a longitudinal edge region of the backsheet.

* * * * *